(12) United States Patent
Chen et al.

(10) Patent No.: US 12,383,458 B2
(45) Date of Patent: Aug. 12, 2025

(54) MEDICAL VEST AND USING METHOD THEREOF

(71) Applicant: Chia-Hung Chen, New Taipei (TW)

(72) Inventors: Chia-Hung Chen, New Taipei (TW); Chia-Chi Su, Taichung (TW); Yu-Wen Sung, Taoyuan (TW)

(73) Assignee: Chia-Hung Chen, New Taipei (TW)

( * ) Notice: Subject to any disclaimer, the term of this patent is extended or adjusted under 35 U.S.C. 154(b) by 762 days.

(21) Appl. No.: 17/619,833

(22) PCT Filed: Jun. 17, 2020

(86) PCT No.: PCT/CN2020/096592
§ 371 (c)(1),
(2) Date: Dec. 16, 2021

(87) PCT Pub. No.: WO2020/253729
PCT Pub. Date: Dec. 24, 2020

(65) Prior Publication Data
US 2022/0354736 A1 Nov. 10, 2022

Related U.S. Application Data

(60) Provisional application No. 62/862,690, filed on Jun. 18, 2019.

(51) Int. Cl.
*A61H 23/02* (2006.01)

(52) U.S. Cl.
CPC ..... *A61H 23/02* (2013.01); *A61H 2201/1621* (2013.01); *A61H 2201/5002* (2013.01); *A61H 2201/501* (2013.01); *A61H 2201/5058* (2013.01)

(58) Field of Classification Search
CPC ............ A61H 9/00–0007; A61H 9/005; A61H 9/0078; A61H 23/00; A61H 23/02–04;
(Continued)

(56) References Cited

U.S. PATENT DOCUMENTS

| | | | | |
|---|---|---|---|---|
| 5,479,661 A | * | 1/1996 | Fingleson | G09B 23/28 434/257 |
| 2008/0108914 A1 | * | 5/2008 | Brouqueyre | A61H 9/0078 601/2 |

(Continued)

FOREIGN PATENT DOCUMENTS

| | | |
|---|---|---|
| CN | 202113310 A | 1/2012 |
| CN | 104055664 A | 9/2014 |

(Continued)

*Primary Examiner* — Rachel T Sippel
(74) *Attorney, Agent, or Firm* — Troutman Pepper Locke LLP; Tim Tingkang Xia, Esq.

(57) ABSTRACT

A medical vest and using method thereof. The medical vest has a cloth capable of surrounding the chest of a user's body, one or more vibration devices located in the cloth respectively and a motion sensor located in the cloth. Hence, when a user wears the medical vest and/or when the user actives one or more vibration devices to apply a net vibration force to the users' chest, the motion sensor may detect the user's real posture and/or both the vibration intensity and/or the vibration frequency of the vibration force applied to the user's chest. Accordingly, the user may adjust the vibration intensity and/or the vibration frequency of one or more vibration devices, also may adjust how the cloth is worn on the user's chest.

12 Claims, 10 Drawing Sheets

(58) Field of Classification Search
CPC ........................ A61H 2201/1619–1626; A61H 2201/5064–5069; A61H 2201/5076; A61H 2201/5084; A61H 2205/08; A61H 2205/084; A61H 2230/62–625
See application file for complete search history.

(56) References Cited

U.S. PATENT DOCUMENTS

| | | | |
|---|---|---|---|
| 2016/0274162 A1 | 9/2016 | Freeman et al. | |
| 2017/0156976 A1 | 6/2017 | Shockley, Jr. et al. | |
| 2017/0266050 A1* | 9/2017 | Morehouse | A61F 11/00 |
| 2018/0177483 A1* | 6/2018 | Ye | A61H 23/004 |
| 2018/0356890 A1* | 12/2018 | Zhang | G06F 3/014 |
| 2019/0038502 A1* | 2/2019 | Shockley, Jr. | A61H 23/02 |
| 2019/0133801 A1* | 5/2019 | Burnett | A61F 5/0003 |
| 2019/0274919 A1* | 9/2019 | Lee | A61H 23/04 |
| 2020/0100981 A1* | 4/2020 | Bobey | A61H 23/0263 |
| 2020/0168312 A1* | 5/2020 | Kang | A61M 16/04 |
| 2020/0219615 A1* | 7/2020 | Rabin | G16H 50/30 |
| 2020/0315894 A1* | 10/2020 | Churilla | A61H 1/00 |
| 2020/0375841 A1* | 12/2020 | Owusu | A61H 15/02 |
| 2023/0056977 A1* | 2/2023 | Ishac | A61B 5/742 |

FOREIGN PATENT DOCUMENTS

| | | | |
|---|---|---|---|
| CN | 205286895 U | 6/2016 | |
| CN | 107812373 A | 3/2018 | |
| CN | 109833193 A | 6/2019 | |
| KR | 20110138893 A | 12/2011 | |

* cited by examiner

| posture | description | direction | altitude | motion sensor ||| 
| | | | | gravity force(m/s²) | magnetic force(μT) | acceleration (m/s²) |
|---|---|---|---|---|---|---|
| 1 | anterior upper section (upper leaf) | X | 15~32 | -1~5 | | -2~5 |
| | | Y | 35~60 | | -60~-30 | -12~-5 |
| | | Z | | | | -9~0 |
| 2 | posterior section | X | | -5~1 | | -6~6 |
| | | Y | 21~75 | -10~-2 | | -13~-2 |
| | | Z | | 3~9 | 30~57 | 0~14 |
| 3 | anterior section | X | -3~15 | -1~3 | | -2~5 |
| | | Y | -5~27 | -6~-2 | -40~-6 | -5~3 |
| | | Z | | -11~-7 | -60~-28 | -14~-6 |
| 4 | right posterior section | X | -81~-61 | -10~-7 | -66~-28 | -15~-3 |
| | | Y | -10~11 | -3~3 | -44~-2 | -5~5 |
| | | Z | | -5~0 | | -6~1 |
| 5 | left posterior section | X | 30~160 | 3~9 | 5~45 | -3~13 |
| | | Y | -21~25 | -2~4 | -32~-1 | -5~8 |
| | | Z | | 4~10 | 13~65 | |
| 6 | middle right section | X | -49~17 | | -51~-15 | -8~3 |
| | | Y | -24~3 | -3~4 | -12~6 | -5~4 |
| | | Z | | -10~-5 | -55~-35 | -12~-6 |
| 7 | left tongue | X | 50~95 | 6~11 | 5~70 | 3~15 |
| | | Y | -14~25 | -3~3 | -35~-5 | -6~5 |
| | | Z | | -7~0 | | -5~2 |
| 8 | anterior section (lower leaf) | X | 8~37 | 1~8 | | -4~6 |
| | | Y | -25~5 | -1~4 | | -2~7 |
| | | Z | | -10~-5 | -55~-38 | -14~-4 |
| 9 | right segment section | X | -75~-45 | -10~-6 | -72~-25 | -16~-3 |
| | | Y | -32~-3 | -1~4 | -25~-5 | -4~6 |
| | | Z | | -8~-3 | | -7~2 |
| 10 | left segment section | X | 65~135 | 7~10 | 20~55 | 2~19 |
| | | Y | -20~25 | -4~2 | -35~-3 | -2~9 |
| | | Z | | | | -2~10 |
| 11 | posterior section | X | | | | -12~8 |
| | | Y | -17~17 | -1~5 | | -9~8 |
| | | Z | | 2~10 | | -4~14 |
| 12 | upper section | X | -180~180 | -3~3 | | -5~4 |
| | | Y | -7~20 | -3~2 | | -5~5 |
| | | Z | | 8~11 | 30~75 | 6~14 |

FIG. 4B

MEDICAL VEST AND USING METHOD THEREOF

FIELD OF THE INVENTION

The present invention relates to a medical vest and using method thereof, and more particularly to a medical vest that both the motion sensor and the vibration device in the cloth of the medical vest and its using method.

BACKGROUND OF THE INVENTION

The medical vest has been popularly applied to treat the patients with thoracic diseases, especial to treat the patients whose tracheal system and lungs are prone to accumulation of sputum, mucus or debris but whose body is not easy to remove these through cough or mucociliary movement. The basic mechanism of the vest chest is regularly applying force, such as high frequency pressure pulse, to the chest cavity of the patient who can not continuously apply sufficient force to remove sputum, mucus or debris by himself. Hence, an external force is applied to the patient's body such that sputum, mucus or debris are removed from lungs and tracheal system. During the past recent years, the medical vest has been popularly applied to treat patients with at least one of the following diseases: bronchiectasis, cystic fibrosis, chronic bronchitis, pneumonia, whooping cough, chronic obstructive pulmonary disease, asthma, ciliary immobility syndrome, breathing distress syndrome.

The existing commercial medical vests may be divided into two main categories according to how the force is applied to the patient's body: the gas vibration type and the mechanical vibration type. The former uses the pump to deliver gas through the pipeline(s) surrounding the patient's body, so that the gas is pumped and delivered regularly and continuously apply the vibration force to the patient's body. The later places a machine, such as the brush motor or the brushless motor, on the medical vest, so that the motor vibrates regularly and continuously apply the vibration force to the patient's body. No matter the former or the latter, it may be viewed as that the medical vest has one or more vibration devices capable of continuously apply the vibration force to the patient's body wearing the medical vest.

Generally speaking, the existing commercial medical vests are used by nurses, physicians, respiratory therapists or other medical professionals who adjust each patient's body posture according to the patient's physical condition, or are used by the patient himself to adjust his own body posture by referring to the posture instructions. Apparently, none of them can accurately determine the body posture of the patient wearing the medical vest, especially there is no way to check the position of the medical vest relative to the patient's body (or viewed as there is no way to check whether the vibrating part(s) of the medical vest correctly corresponds to the parts of the patient's body requires the applied forces). Indeed, the human body senses are always not perfectly precise, also there is no way to judge whether the patient wears properly the medical vest while the medical vest applies the vibration force to the patient' body.

Moreover, the existing commercial medical vests may be used by the medical professionals such as nurse, physicians or respiratory therapists, wherein the medical professions decide the intensity of the vibration force applied to the patient's body by directly touching the medical vest or the patient's body. The existing commercial medical vests also may be used by the patient himself to directly feel and judge the vibration force applied to his body. Apparently, none of them can accurately determine the actual intensity of the vibration force applied to the patient's body, especially none of them can accurate determine the difference between the intensity of the vibration force applied by the medical vest and the intensity of the vibration force felt by the patient's body wearing the medical vest. Indeed, the human body senses are always not perfectly precise, also there is no way to judge the difference between the intensity of the vibration force applied by the medical vest and the intensity of the vibration force felt by the patient's body wearing the medical vest. In addition, the tightness of the medical vest also affects the intensity of the vibration applied by the medical vest to the patient's body.

Accordingly, it is required to develop new medical vest and new using method so as to improve some disadvantages of the existing commercial medical vest.

SUMMARY OF THE INVENTION

The proposed invention provides a medical vest whose basic structure includes one cloth, one or more vibration devices and one motion sensor. The cloth is worn by a user (such as a patient) on the chest cavity of the user's body. Different vibration devices are located at different positions of the cloth to apply different vibration forces to different portions of the user's chest. The motion sensor is also located in the cloth to detect the actual vibration force appeared on the cloth (or viewed as appeared on the users' chest close to the cloth).

Significantly, the main technical feature of the proposed medical vest is the usage of the motion sensor. Because the motion sensor detects the vibration force appeared in the cloth as well as the movement (such as speed, acceleration or direction) of the cloth, the usage of the motion sensor real-time detects the vibration force applied to the medical chest (or viewed as to the chest of the user's body wearing the medical vest) without referring to the human body senses of the medical professional and/or the patient. Thus, the proposed medical vest improves the following disadvantages of the existing commercial medical vest: the applied vibration force must be determined before it is used by the patient and the practical vibration force appeared on the medical vest only may be detected by the human body senses of the medical professional and/or the patient. Moreover, by using the motion sensor, the postures (or viewed as the postures of the body of the patient wearing the medical vest) may be detected without referring to the human body sense of the patient and/or the medical professionals, and then may improve the disadvantages of the existing commercial medical vest that can not provide the messages required to check the body postures.

The proposed medical vest only uses the motion sensor to detect the intensity and/or the frequency of the vibration force appeared in the cloth, even to detect the body posture of the patient wearing the proposed medical vest. To compare with some existing applications of the motion sensors such as shooting of movie special effect and studying of sports science, the proposed invention does not require such more detected items and such high detection precision. Therefore, the present invention needs not to further limit the motion sensor, such as multi-axis sensors, magnetometers and/or accelerometers. Any existing, developing and future motion sensors may be used, also there is no need to develop any new motion sensor.

In the proposed medical vest, in order to reduce noise during the detecting process, a motion sensor is usually separated from one or more specific vibration devices when the motion sensor is used to detect the special vibration device(s). For example, a common way is to place a motion sensor and a specific vibration device in the cloth while their positions are separately symmetrical to the center line of the cloth and located in the same side of the cloth along a direction vertical to the center line. The common way also may be viewed as that the motion sensor and the special vibration device are placed horizontally symmetrical to the spine of the human body wearing the medical vest and are all placed in the front chest or the back of the human body. Of course, if necessary, the present invention optionally place two or more motion sensors at different portions of the cloth at the same time, so as to detect the vibration force applied by one or more vibration devices placed in the cloth simultaneously.

In the proposed medical vest, in order to reduce the performance degradation or even the damage of the motion sensor caused by the continuous vibration of the vibration device(s), any vibration device is optionally fixed in the cloth and any motion sensor is optionally removable from the cloth. In this way, one more motion sensors are installed in the cloth to detect when the user needs to wear the medical vest and to adjust the vibration force applied to the user's body by the medical vest. After the user properly wears the medical vest and adjust the operation of each vibration device to provide vibration force with appropriate vibration intensity and vibration frequency, one or more motion sensors are optionally to be removed from the cloth.

The proposed invention also presents a method for using a medical vest, which includes the following basic steps. First, use the motion sensor located in the medical vest to detect the vibration force applied to the body of the user wearing the medical vest by at least one vibration device located in the medical vest. Then, use the transmission module located in the medical vest to transmit the message detected by the motion sensor to a control device. Finally, use the control device to adjust at least one of the following according to at least the message detected by the motion sensor and the at least one user body message: the vibration frequency and/or vibration intensity of the at least one vibration device, and how the medical vest is worn on the use's body.

Optionally, the present method of the medical vest places both of the motion sensor and the vibration device on the medical vest where their positions are symmetrical to the vertical center line and on the same side (front side or back side) when only one vibration device is used. In this way, the intensity and/or the frequency of the vibration force generated by the vibration device may be more accurately detected. Of course, when multiple vibration devices are used to provide multiple vibration forces at the same time, it is optional to use these vibration devices in turn, where the motion sensor and these vibration devices are placed symmetrical to the vertical center line and on the same side (front side or back side) of the medical vest in turn. In this way, the intensity and/or the frequency of the vibration force generated by each of these vibration devices may be more accurately detected in turn.

Optionally, the present method for using medical vest allows a specific vibration device to sequentially provide a variety of different vibration forces during different test periods and to use both the motion sensor and the transmission module to transmit the detected message in turn to the control device. After that, a specific vibration force is selected based on the experience of the user wearing the medical vest and/or the evaluation result of the medical professional, and then the specific vibration device is adjusted through the control device to continually provide the specific vibration force in the subsequent medical period.

Optionally, the present method for using medical vest allows a motion sensor to detect an initial body posture message right after a user just wears a medical vest. After that, a to-be-treated body posture message is detected by the motion sensor right after the user adjust its body posture such that the medical vest may apply the vibration force to his chest, so as to decide whether the user has properly adjusted his body posture to a required special to-be-chest-treated body posture and to adjust the applied vibration force.

BRIEF DESCRIPTION OF THE DRAWINGS

Other advantages, objectives and features of the present invention will become apparent from the following description referring to the attached drawings.

FIG. 4A and FIG. 4B are the auxiliary diagrams of some embodiments of the method of using the medical vest.

DETAILED DESCRIPTION OF THE INVENTION

Figure 1A:
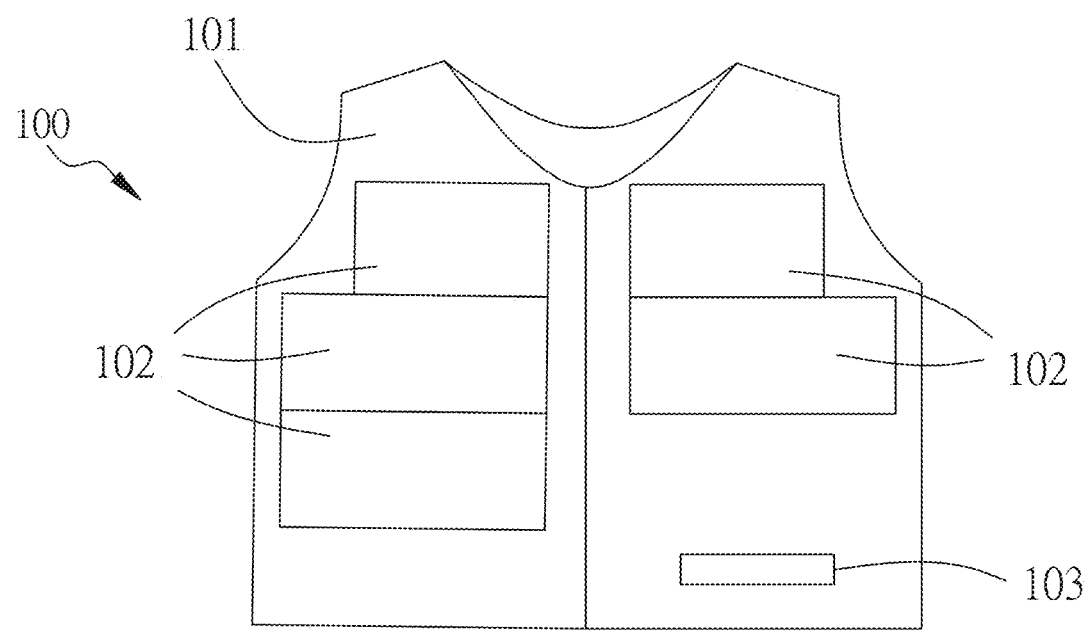
FIG. 1A to FIG. 1E schematically illustrates the structure of the medical vest by referring to some embodiments respectively.
Figure 1B:
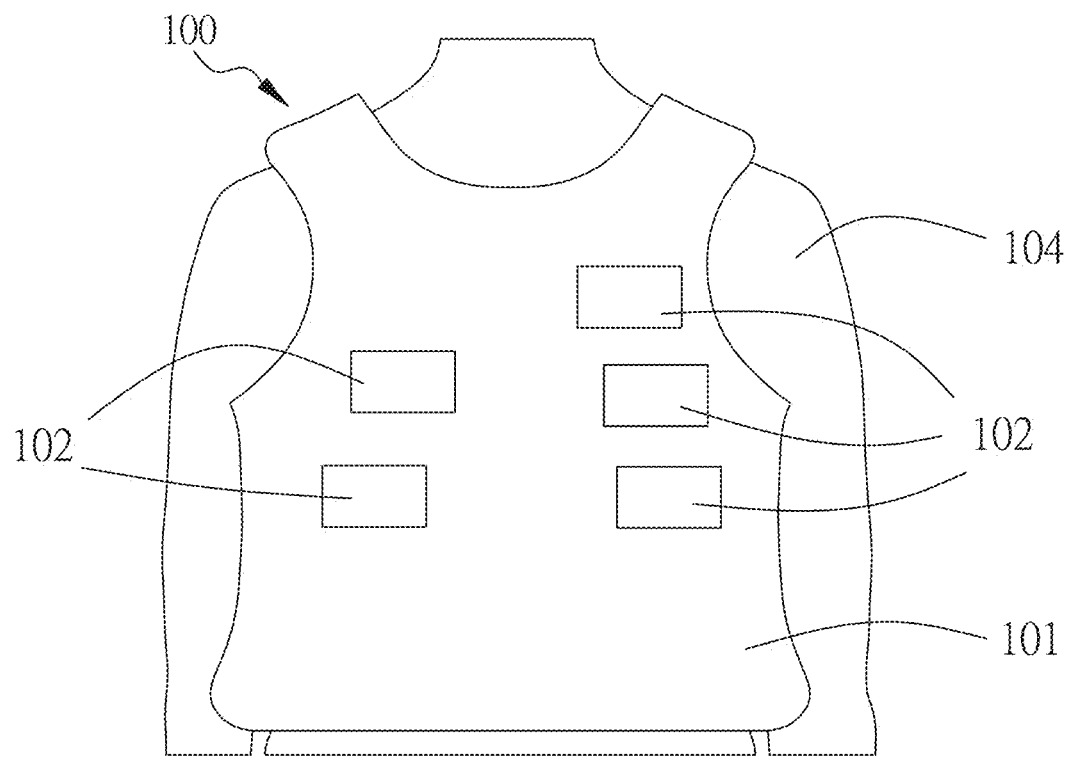

Some embodiments of the invention are related to the medical vest. As the front view of the medical vest shown in FIG. 1A and as the back view of the medical vest worn on the body of a user shown in FIG. 1B, such medical vest 100 at least includes one cloth 101, one or more vibration devices 102 and one motion sensor 103. The cloth 101 is configured to be worn on at least a vest cavity of the user's body, one or more vibration devices 102 are placed at one or more positions in the cloth 101 and correspond to the user's vest cavity, also the motion sensor 103 is placed in the cloth 101. To compare with the existing commercial medical vest, the main feature of these embodiments is the usage of the motion sensor 103, especially the motion sensor 103 placed in the cloth 101 to be worn by the user like the vibration device(s) 102. In this way, the motion sensor 103 capable of detecting at least one of the following: the body posture of the user's body 104, the vibration frequency of the vibration force applied to the chest by at least one vibration device 102, and the vibration intensity of the vibration force applied to the chest by at least one vibration device 102.

Apparently, since both the vibration device(s) 102 and the motion sensor 103 are placed in the cloth 101, the motion sensor 103 is capable of detecting the vibration intensity and/or vibration frequency of the vibration force appeared in the cloth 101, or viewed as being capable of detecting the vibration intensity and/or vibration frequency of the vibration force applied to the user's body 104. In contrast to the existing commercial medical vest that the vibration intensity and/or the vibration frequency only may be pre-determined, the medical vest 100 present by these embodiments may more accurately monitor the practically applied vibration force by the usage of the motion sensor 103. Note that the non-negligible difference between the practical vibration force applied to the user's chest cavity and the pre-determined vibration force to be applied by the medical vest 100 usually is unavoidable. It is attributed to but not limited to at least one of the following factors: whether the user wears properly the medical vest 100, whether the user fastens tightly or slightly the medical vest 100 to the user's body, and whether the vibration device(s) applies precisely the pre-determined vibration force.

Apparently, since both the vibration device(s) 102 and the motion sensor 103 are placed in the cloth 101, the motion sensor 103 is capable of detecting the generated vibration force in a real-time manner when at least one vibration force generates the vibration force, especially by using the mechanical component(s) and/or electronic component(s) inside the motion sensor 103 to detect the appeared vibration force. In contrast to the existing commercial medical vest that the vibration force applied by the existing commercial medical vest only may be detected by the user who feels the pain degree when the existing commercial medical vest shaking the chest cavity or by the medical professional who touches the user's chest and/or back with his hand to feel the vibration force, the present medical vest 100 may provide the objective detected result to the patient and/or the medical professional as a reference for subsequent adjustments without referring to the human body sense of the patient and/or the medical professional, even may cover the variety results when the user wears the medical vest 100 with different tightness. Particularly, the real-time message related to the vibration force may be provided to the patient and/or the medical professional for adjusting the operation of the medical vest 100 before the improper vibration force hurts the patient (or viewed as the user) or induces no useful curative result.

Figure 1C:
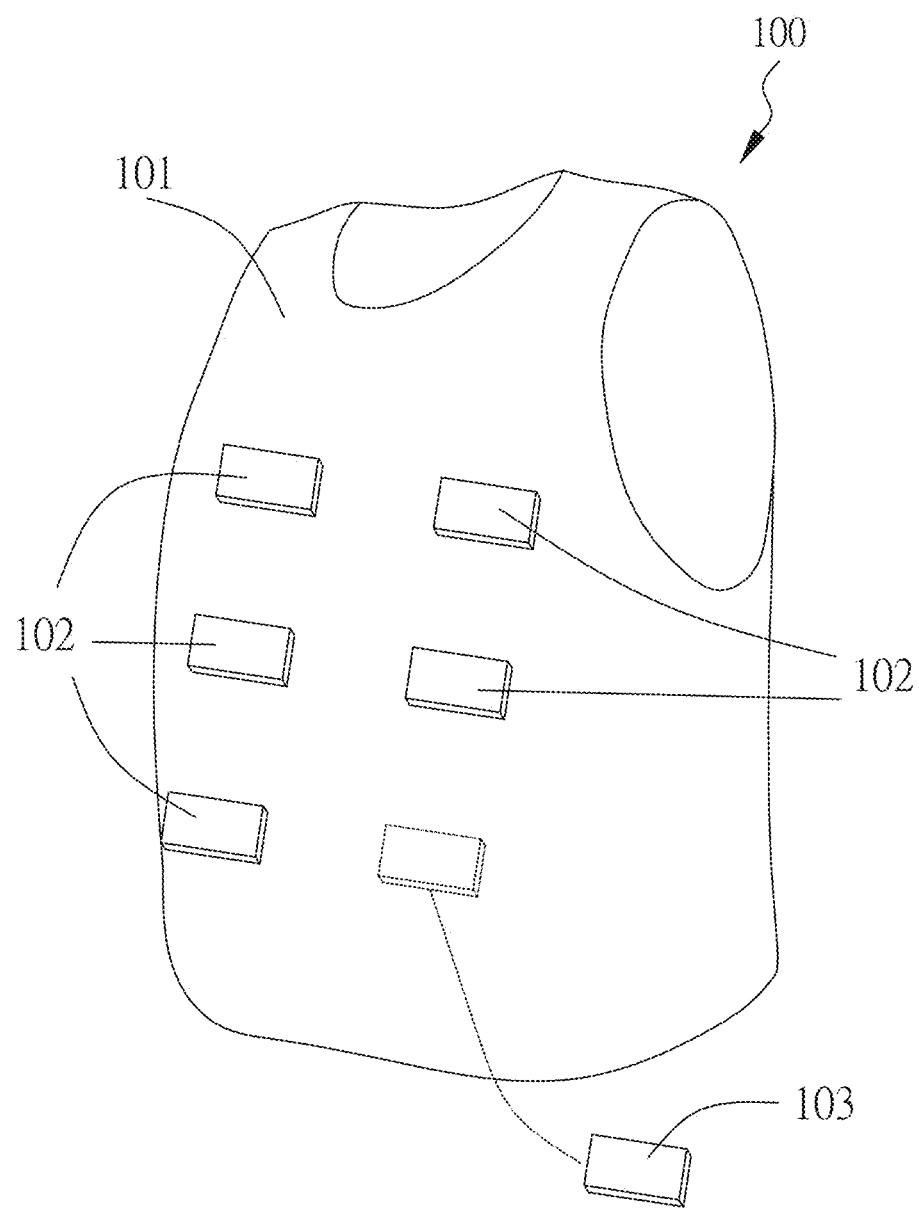

Furthermore, among different embodiments, the motion sensor 103 usually is separated away a specific vibration device 102 when the motion sensor 103 is used to monitor the specific vibration device 102. Also, each vibration device 102 usually is fixed in the cloth 101 but the motion sensor 103 usually is removable from the cloth 101. The reason is that any vibration force generated during the operation of any vibration device 102 acts unavoidably on the motion sensor 103 placed in the cloth 101, and then induces noise during the period that the motion sensor 103 detects the practical vibration force appeared in the cloth 101 or even damage the motion sensor 103 due to the continuous vibration. Hence, a finite distance between the motion sensor 103 and one or more vibration devices 102 configured to generate the vibration force(s) may reduce the impact of the noise and protect the motion sensor 103. Particularly, because the existing commercial vibration device(s) 102 may provide continuously a specific vibration force with specific vibration frequency and/or specific vibration intensity for quite some after being set up to provide such specific vibration frequency. If the motion sensor 103 is detachable as shown in FIG. 1C, it is optional to place the motion sensor 103 in the cloth 101 or to separate the motion sensor 103 away the cloth 101 as needed. For example, the motion sensor 103 is optionally placed in the cloth 101 to detect different vibration forces generated by one or more vibration device 102 respectively, and the motion senor 103 is optionally removed away the cloth 101 after the detection by the motion sensor is finished and the operation of the one or more vibration devices has been adjusted properly.

Figure 1D:
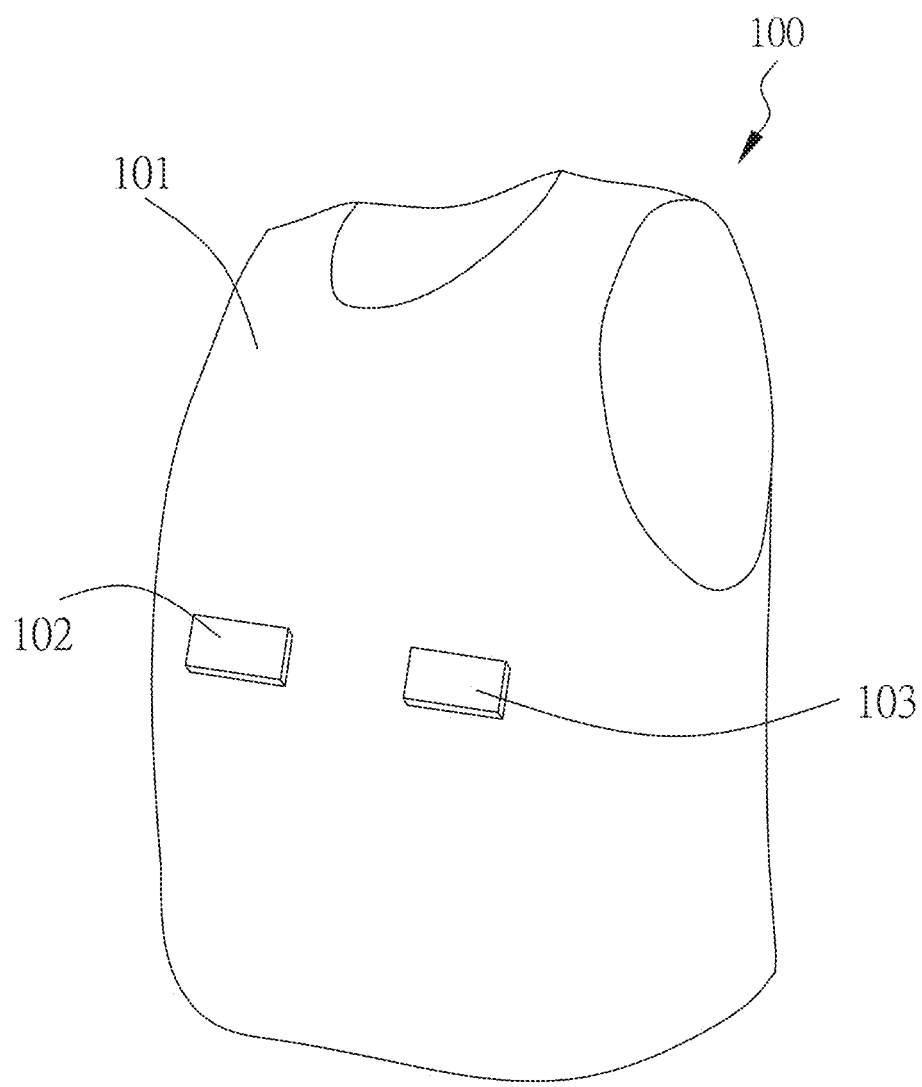

In some different embodiments, several motion sensors 103 are placed in the cloth 101 simultaneously, wherein different motion sensors 103 may operate together or separately. For example, if two motion sensors 103 are placed in the front chest and the back of the user's body respectively, the two motion sensors 103 may be used to detect different vibration forces appeared on the front chest or the back respectively without disassembling the same motion sensor 103 and placing it on the front side (or viewed as front chest) and the back side (or viewed as back) of the cloth 101 respectively. In addition, in different embodiments, the relative position between the motion sensor 103 and the vibration device 102 right generates the vibration force to be detected is optionally different, each may be adjusted according to the practical requirement. One popular situation is shown in FIG. 1D, the positions of the motion senor 103 and the specific vibration device 102 in the cloth 101 are symmetrical to the center line of the cloth 101 and are placed in the front side (or the back side) at the same time, which may be viewed as being symmetrical to the spine of the user's body 104 covered by the cloth 101 and all located in the user's front chest or the user's back.

In some different embodiments, different vibration devices 102 are generally located at different positions in the body 101 and usually vibrate respectively. It is optional to active only one or more of a number of vibration devices to apply one or more vibration forces to the user's body 104, and the vibration frequency and/or the intensity of the vibration force generated by any active vibration device 102 is optionally independent on that generated by any other active vibration device 102. In this way, the medical vest 100 proposed by this invention is very suitable when different users have to use the same medical vest 100 to apply different vibration forces to different portions of their chest cavities respectively for treating the individual lesions induced by sputum, mucus and debris, or when a single user has to treat different lesions appeared in different portions of his chest cavity.

Figure 1E:
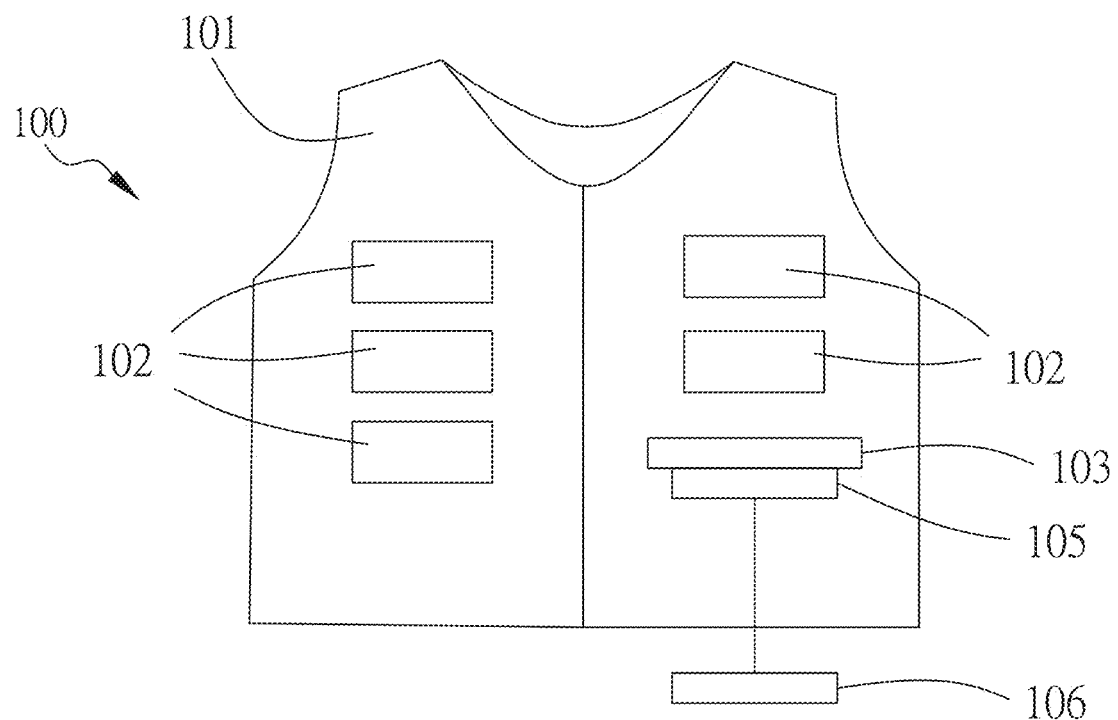

Furthermore, as shown in FIG. 1E, in some different embodiments, the medical vest 100 further includes the transmission module 105 configured to transmit any message detected by the motion sensor 103 to the control device 106, such that the user may adjust how the medical vest 100 is worn and how the vibration force is generated by the medical vest 100. For example, the user may adjust the vibration frequency and/or the vibration intensity of at least one vibration device 102, so as to adjust the vibration force applied to the cloth 101 and/or the user's body 104. For example, the user may adjust how the medical vest 100 is worn on the user's body 104, such as tightening the cloth 101 to the user's body 104 or replacing the used one with a new medical vest having a larger size. In general, in order to decrease any damage may be induced by the vibration force generated by the vibration device 102 also in order to co-work with the popular mobile devices and the internet of things (IoT), the control device 106 is placed outside the medical vest 100 and is integrated into a device, such as mobile phone, tablet, laptop and/or table computer, with installed controlling applications. Optionally, the transmission module 105 is Bluetooth® module, Wi-Fi module, infrared module and/or cable line module, wherein a popularly used transmission module 105 is the Bluetooth® module having wide bandwidth, long transmission distance and ability of wireless transmission. Although the motion sensor 103, the transmission module 105 and the control device 106 are placed in the same circuit board in the cloth 101 for some embodiments when only considers the main feature of using the motion sensor 103 to detect the vibration force generated by the vibration device 102.

In some different embodiments, it is not necessary to specifically limit the hardware details of the cloth 101, the vibration device 102 and the motion sensor 103. Each of them may be implemented by using any currently existed, on-developed and to-be-appeared hardware, especially may be implemented by mainly using the commercial products. For example, the cloth 101 may be a vest, a polo shirt, a T-shirt and so on, and both the vibration device 102 and the motion sensor 103 may act on the patient's chest after the patient wears the cloth 101. For example, each vibration device 102 may be a brush motor, a brushless motor, a stepping motor or a pipeline connected to a pump. That is to say, the main technical feature may be to applied to the medical vest 100 with mechanical vibration and also to the medical vest 100 with gas shocking. For example, the motion sensor 103 may be a multi-axis sensor, a magnetometer and/or an accelerometer, depending on whether the main requirement is to detect the intensity and/or frequency of the vibration force or whether it is to detect the body posture of the user wearing the medical vest 100.

In addition, some other non-illustrated embodiments are related to other possible variations. For example, one or more vibration devices 102 are placed in multiple pockets of the cloth 101. Here, the size of any pocket may be equal to the size of the corresponding vibration device 102, so as to tightly fix the position of the vibration device 102 in the cloth 101. However, the size of any pocket also may be larger than the size of the corresponding vibration device 102, such that the position of the vibration device 102 in the user's body is adjustable within the size of a pocket. As usual, one or more vibration devices 102 placed in the cloth 101 may be distributed much more in the front side of the cloth 101 (corresponding to the front chest of the user) than that in the back side of the cloth 101 (corresponding to the back of the user). In this way, the vibration force is fully applied to the tracheal system whose distribution on the back of the human body is more than that on the front chest of the human body. For example, in order to reduce the negative effect of the vibration force on the heart, the position of the vibration device 102 may be closer to the edge of the clothing body in the part of the clothing body corresponding to the left half of the human body. For example, in order to reduce the probability of vibration force being applied to parts of the human body other than the lungs and tracheal system, the position of the vibration device 102 in the cloth 101 is not lower than the rib cage or adjacent to the abdominal cavity (abdomen) after the user wearing the medical vest 100.

Surely, in order to simplify both the drawings and the discussion, the details of the technical feature of the proposed medical vest 100 are omitted here. For example, in some embodiments, a hook or loop fastener is present on the shoulder of the cloth 101, so that the size of the entire medical vest 100 is adjustable. For example, in some embodiments, some zippers or buttons are placed in the front half of the cloth 101 to adjust the tightness of the medical vest 100 worn on the user's body 104.

Figure 2A:
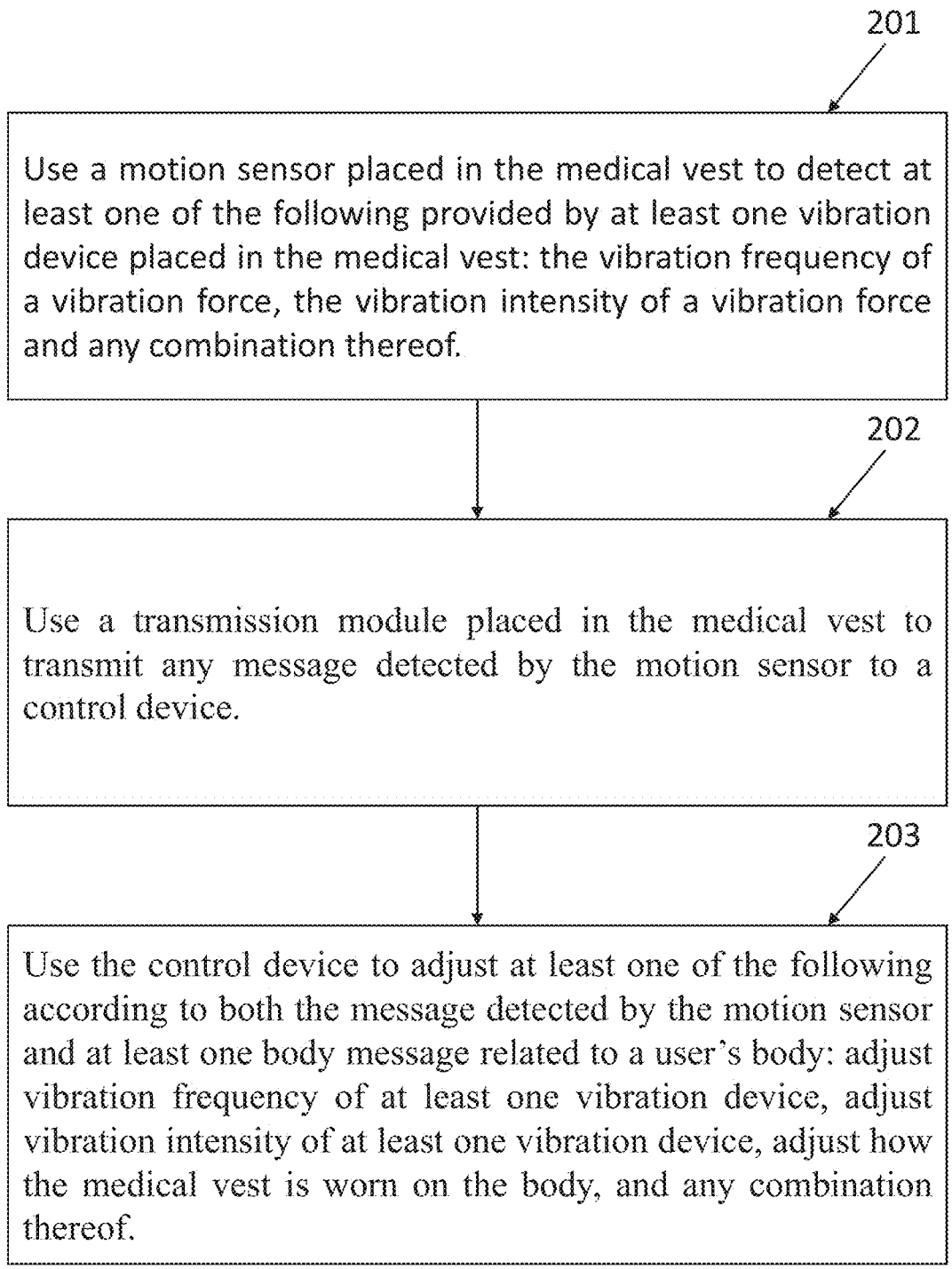
FIG. 2A to FIG. 2B presents the flowchart of the method of using the medical vest by referring to some embodiments respectively.

Some more embodiments of the invention are related to a method of using the medical vest which has the following essential steps as shown in FIG. 2A. First, as shown in step block 201, use a motion sensor placed in the medical vest to detect at least one of the following provided by at least one vibration device placed in the medical vest: the vibration frequency of a vibration force, the vibration intensity of a vibration force and any combination thereof. Then, as shown in step block 202, use a transmission module placed in the medical vest to transmit any message detected by the motion sensor to a control device. Finally, as shown in step block 203, use the control device to adjust at least one of the following according to both the message detected by the motion sensor and at least one body message related to a user's body: adjust vibration frequency of at least one vibration device, adjust vibration intensity of at least one vibration device, adjust how the medical vest is worn on the body, and any combination thereof. Here, the user's body message may include user's body height, the user's body weight, the user's age and the user's gender, or other message related to the user's body, such as body fat percentage and chest circumference length and many more. Cleary, the key point is to initially use the motion sensor to detect the vibration force generated by the vibration device, and then to transmit the detected message to the control device through the transmission module so that the patient and/or the medical professionals may adjust the usage of the medical vest accordingly. Specially, how the motion sensor, the one or more vibration devices, and the transmission module (or even the control device) are integrated as a part of the medical vest is not limited herein. Similarly, the details of each of the used hardware also is not limited too.

Figure 2B:
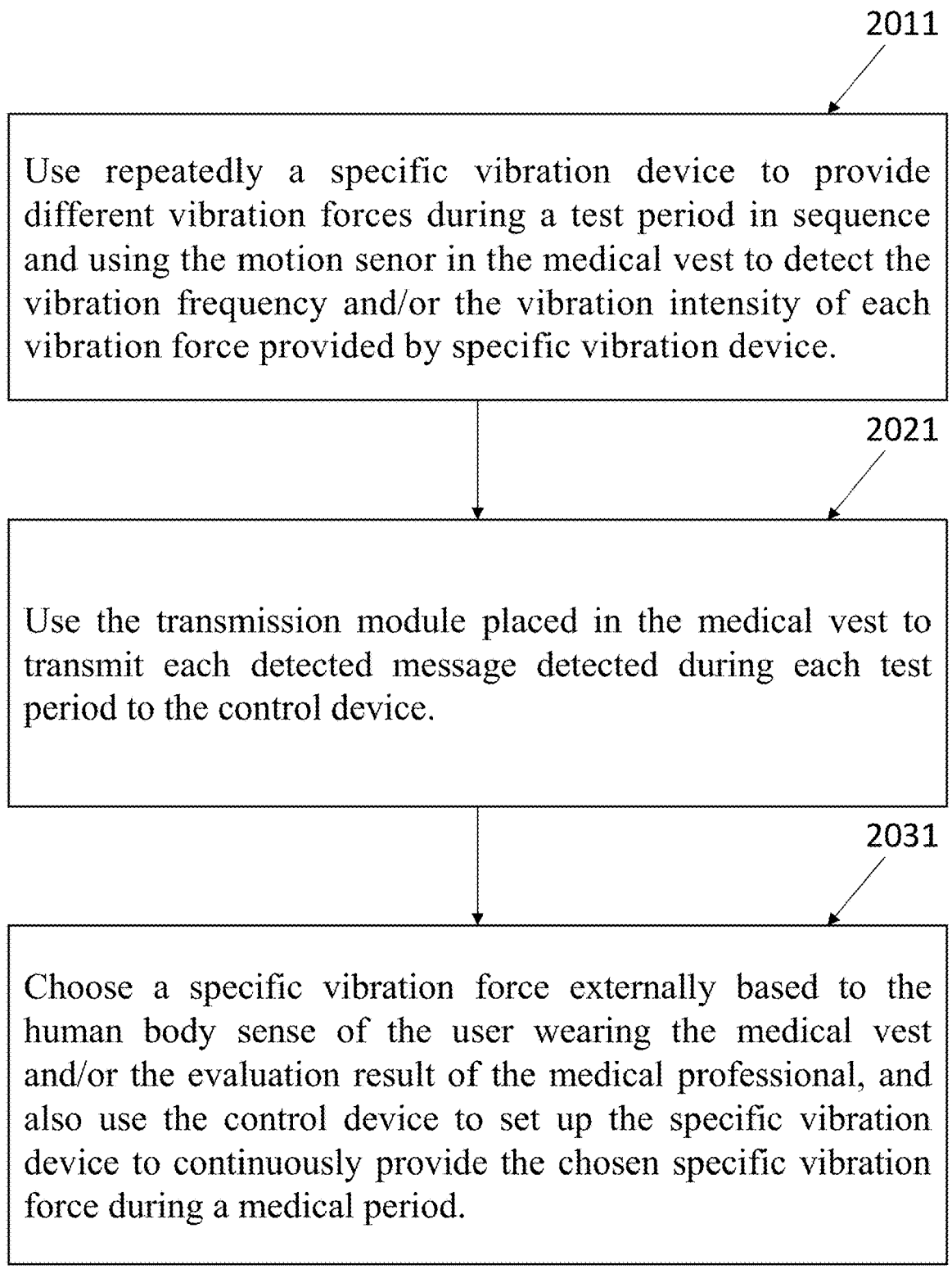

Further, in order to adjust the setting of the vibration force according to the difference between the vibration force actually applied to the medical vest (or the body of the user wearing the medical vest) measured by the motion sensor and the vibration force that the vibration device is set to generate, some other embodiments include at least the following basic steps as shown in FIG. 2B. First of all, as shown in block 2011, use repeatedly a specific vibration device to provide different vibration forces during a test period in sequence and using the motion senor in the medical vest to detect the vibration frequency and/or the vibration intensity of each vibration force provided by specific vibration device. Then, as shown in block 2012, use the transmission module placed in the medical vest to transmit each detected message detected during each test period to the control device. Finally, as shown in block 2013, choose a specific vibration force externally based to the human body sense of the user wearing the medical vest and/or the evaluation result of the medical professional, and also use the control device to set up the specific vibration device to continuously provide the chosen specific vibration force during a medical period. Of course, in some embodiments not particularly shown in any figure, it is optional to use the control device to set up the specific vibration device to continuously provide a lightly adjusted specific vibration force during a medical period when the corresponding vibration frequency and/or vibration intensity is lightly adjusted initially after the specific vibration force is chosen. For example, a specific vibration device is operated during ten test period when different vibration forces with different intensities and/or frequencies are generated by the specific vibration device during different test period, and then the patient and/or the medical professional selects one of the then tested vibration forces to be provided by the vibration device during a sequent medical period according to the patient's body sense and/or the professional evaluation made by the medical professional after all of ten different test results test during these test periods are transmitted to the control device by using the transmission module. Of course, in case of multiple specific vibration devices have to be adjusted and to re-set corresponding vibration forces respectively, it is optional to initially select one of them to run the process shown in step blocks 2011~2031 and then select each of other specific vibration devices in sequence to repeatedly run the process shown in step blocks 2011~2031. After all specific vibration devices have been adjusted well, use these specific vibration devices to apply the vibration forces to the user's body during the medical period.

In addition, although not specifically shown in any figures, in some embodiments, when the control device receives the message sent from the smart stethoscope or the evaluation input by the medical professional that indicates one or more specific portions of the patient's body have sputum, mucus, and/or debris, the control device actives one or more vibration devices corresponding to the one or more specific portions.

Figure 3:
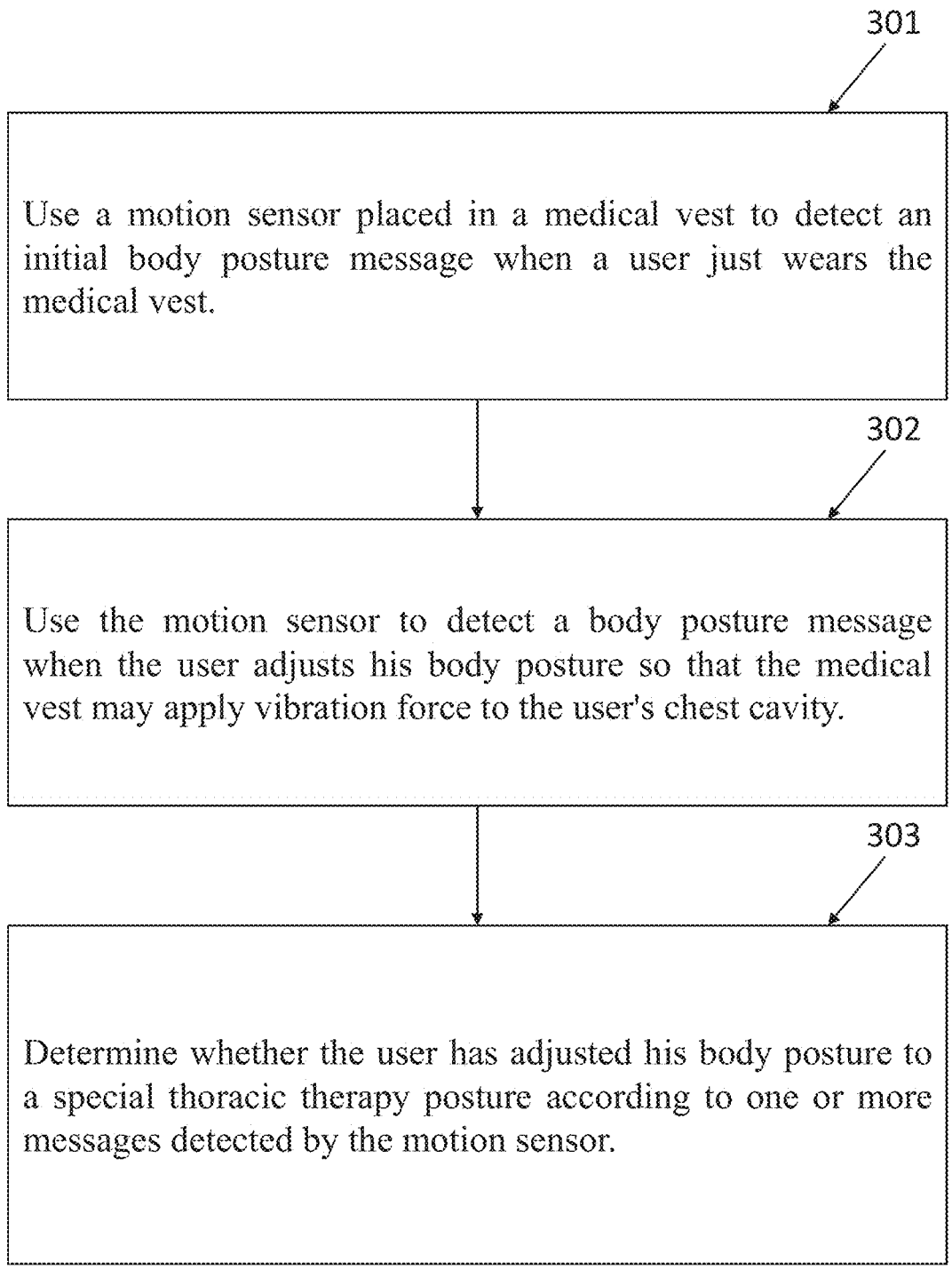
FIG. 3 presents the flowchart of the method of using the medical vest by referring to some embodiments.

Some other embodiments of the proposed invention are related to a method of using the medical vest, which include at least the following base steps as shown in FIG. 3. Initially, as shown in step block 301, use a motion sensor placed in a medical vest to detect an initial body posture message when a user just wears the medical vest. Then, as shown in step block 302, use the motion sensor to detect a body posture message when the user adjusts his body posture so that the medical vest may apply vibration force to the user's chest cavity. Finally, as shown in block 303, determine whether the user has adjusted his body posture to a special thoracic therapy posture according to one or more messages detected by the motion sensor.

Figure 4A:
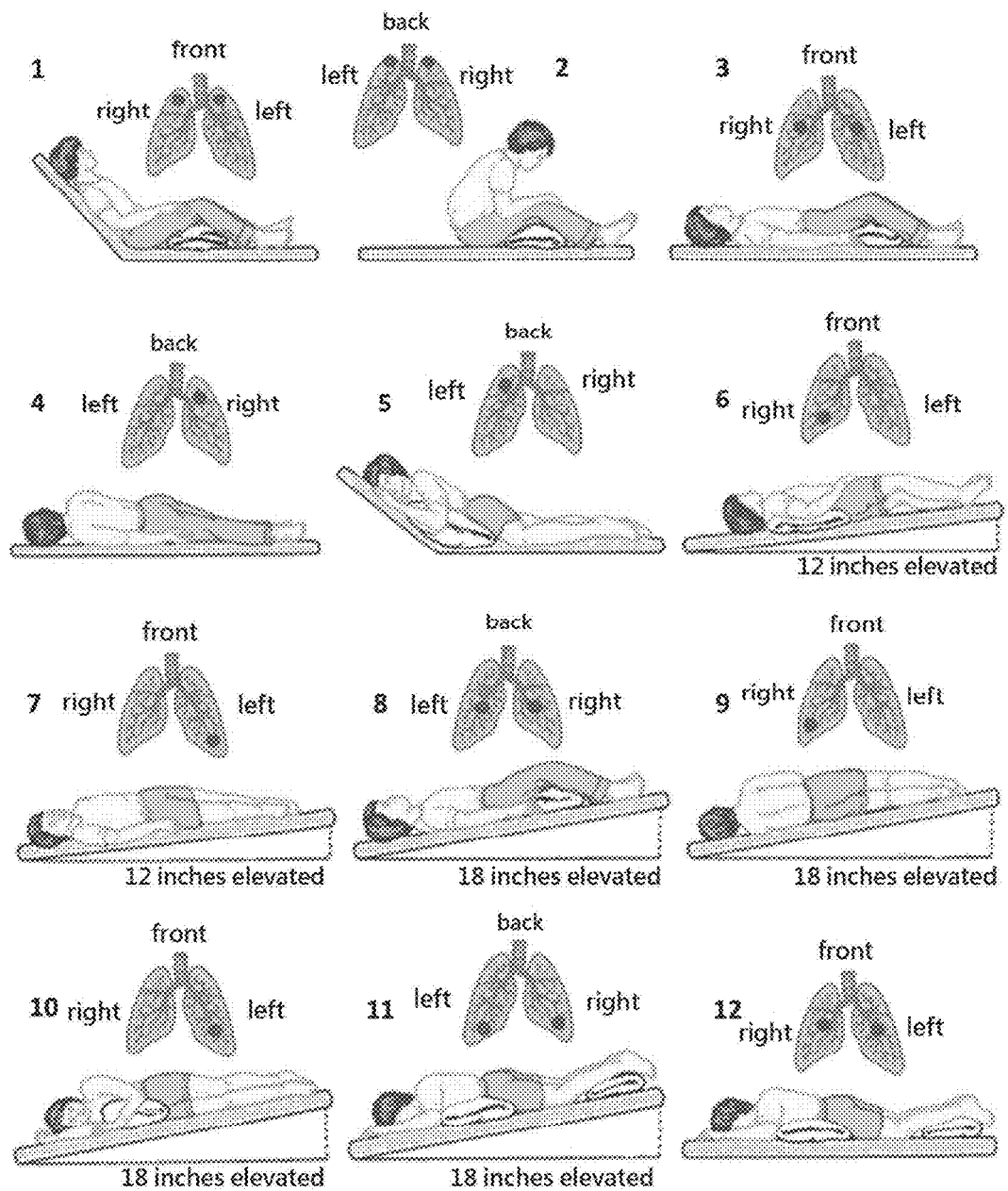

Significantly, because the motion sensor is placed and fixed in the medical vest, the variation of the user's body posture automatically induces the real-time and objective detection of shape and/or position of the medical vest during the period from the user wearing the medical vest until the user taking off the medical vest. No matter the user's body posture is bent forward, tilted backward or turned left and/or right, also no matter whether the user's posture is changed from sitting to standing or lying. In other words, when the user adjusts his body posture to facilitate one or more vibration devices in the medical vest to apply one or more vibration forces to one or more portions of his chest cavity (from front chest and/or the back) which requires external forces to remove sputum, mucus and/or debris, any message detected by the motion sensor in the medical vest may indicate the difference between the user's actual body posture at this time and the more suitable body posture to deal with sputum, mucus and/or debris in a specific chest cavity. In this way, the user may adjust his own body posture accordingly until his body may continuously receive proper vibration force(s) from one or more vibration devices placed in the worn medical vest. Indeed, the current chest physical therapy divides the patient's body posture into twelve chest physical therapy postures when it is required to apply the vibration force to the patient's chest for enhancing the removal of sputum, mucus or debris from the lungs and/or tracheal system, wherein the twelve categories correspond to a distribution of sputum, mucus or debris in the patient's body. Hence, in some embodiments, in order to assist the patient to properly wear the medical vest without the assistance of professional medical personnel, the twelve chest physical therapy postures shown in FIG. 4A as well as shown the recommended motion sensor value table shown in FIG. 4B are attached to the cloth of the medical vest, and the motion sensor detects gravity force, magnetic force and acceleration in x, y and z coordinate directions. In this way, a reference is provided to the user so that he may adjust his body posture to a desired chest physical therapy posture after wearing the medical vest. Therefore, even only refer to the messages shown in FIG. 4A and FIG. 4B without referring to any assistance provided by any nearby medical professional, the patient himself may select a specific chest physical therapy posture based on his own body's sensation or the previous diagnosis indicating which part(s) should be applied vibration force. Then, the patient himself may confirm whether the body posture has been adjusted to be quite compatible with this specific chest physical therapy body posture according to the detected result of the motion sensor. For example, in the situation of using the fifth chest physical therapy body posture, the body posture may be adjusted after the medical vest being worn until the messages detected by the motion sensor are equal to that of the fifth chest physical therapy body posture or the corresponding difference is within the error range (such as the error is within 5%). Then, the user wears the medical vest may maintain his body posture and use the medical vest to apply vibration force to his chest cavity for further removing sputum, mucus and/or debris.

In some embodiment present by the proposed invention and related to the method of using the medical vest, the only hardware requirement is that the motion sensor and each vibration device are located in the cloth of the medical vest. Especially, after the user wears the medical vest, the motion sensor is effectively fixed in the cloth during the process of detecting the vibration force generated by the vibration device and/or the process of detecting the user's body posture change. Among all these embodiments related to the method of using the medical vest, there is no requirement of limit the details of at least each of the vibration device, the motion sensor, the transmission module and the control device, just like the no hardware detail requirement of these medical vest related embodiments present by the proposed invention. For example, the motion sensor and the only one used vibration device are optionally placed symmetrically to the vertical center line of the medical vest and in the same front side (or the same back side) of the medical vest. For example, when multiple vibration devices are placed in the medical vest at the same time, all of these vibration devices are used in turn, and also the motion sensor and any vibration device right in use are placed symmetrical to the vertical center line and on the same front side (or the same back side). Thus, the intensity and/or frequency of the respective vibration force may be adjusted in sequence. On different examples, two different vibration devices are optionally to be placed in two different positions, and two different vibration devices vibrates respectively when the vibration frequency and the vibration intensity of them are independent on each other. Also, at least one vibration device is optional a motor, and the motion sensor is optional a multi-axis sensor, a magnetometer, an accelerometer and any combination thereof. Of course, the motion is optional detachable (or viewed as removable) from different positions in the cloth, the transmission module is optional a wireless communication module, the control device is optional placed outside the medical vest or the control device is optional placed in the medical vest.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A medical vest, comprising:
   one cloth, configured to be worn by a chest of a body;
   one or multiple vibration devices, which are placed at one or multiple positions of the cloth and are adapted to correspond to the chest respectively; and
   one or multiple motion sensors, which are placed in the cloth;

wherein, each vibration device of the one or multiple vibration devices is adapted to apply a force to the body respectively;

wherein, the one or multiple motion sensors are adapted to detect at least one of the following: a body posture of the body, a vibration frequency of a vibration force applied to the chest by at least one vibration device of the one or multiple vibration devices, and a vibration intensity of a vibration force applied to the chest by at least one vibration device of the one or multiple vibration devices;

wherein, the one or multiple motion sensors are adapted to detect the body posture, a gravity force, a magnetic force and an acceleration so as to decide whether the body is properly adjusted to a required particular thoracic therapy posture body posture, wherein each of the gravity force, magnetic force and acceleration are detected in x, y and z coordinate directions.

2. The medical vest according to claim 1, further comprising at least one of the following:

two different vibration devices of the one or multiple vibration devices are placed at two different positions; and the two vibration devices of the one or multiple vibration devices vibrate separately, wherein the vibration frequency and the vibration intensity of the vibration force applied by each of the two vibration devices are independent on the vibration frequency and the vibration intensity of at least one vibration force applied by at least one other vibration device of the one or multiple vibration devices.

3. The medical vest according to claim 1, further comprising using the multiple motion sensors, wherein different motion sensors of the multiple motion sensors are operated separately or together, and wherein each vibration device of the one or multiple vibration devices is fixed in the cloth and each motion sensor of the different motion sensors is removable from the cloth.

4. The medical vest according to claim 1, wherein at least one motion sensor of the one or multiple motion sensors is separated away from a specific vibration device of the one or multiple vibration devices when the at least one motion sensor is used to detect the particular vibration device, and wherein the positions of the at least one motion sensor and the specific vibration device are symmetrical to a center line of the cloth and positioned in the same side of the cloth along a direction vertical to the center line.

5. The medical vest according to claim 1, wherein at least one vibration device of the one or multiple vibration devices is a motor, and wherein the one or multiple motion sensors are chosen from a group consisting of the following: multi-axis sensor, magnetometer, accelerometer and any combination thereof.

6. The medical vest according to claim 1, further comprising a transmission module used to transmit any message detected by at least one motion sensor of the one or multiple motion sensors to a control device, wherein the transmission module is chosen from a group consisting of the following: wire and wireless communications, infrared communication, cable line communication and any combination thereof, and wherein the control device is used to process at least one of the following: adjust vibration frequency of at least one vibration device of the one or multiple vibration devices, adjust vibration intensity of the at least one vibration device, provide at least one message related to how the medical vest is worn on the body, and any combination thereof.

7. A method of using a medical vest, comprising:
a) using a motion sensor placed in the medical vest to detect a body posture, a gravity force, a magnetic force and an acceleration so as to decide whether the body is properly adjusted to a required particular thoracic therapy posture body posture, wherein each of the gravity force, magnetic force and acceleration are detected in x, y and z coordinate directions, and to detect at least one of the following provided by at least one vibration device placed in the medical vest: the vibration frequency of a vibration force, the vibration intensity of a vibration force and any combination thereof;
b) using a transmission module placed in the medical vest to transmit any message detected by the motion sensor to a control device; and
c) using the control device to adjust at least one of the following according to both the message detected by the motion sensor and the at least one body message related to a user's body: adjust vibration frequency of at least one vibration device, and adjust vibration intensity of the at least one vibration device, and to provide an indication of how to adjust a wearing manner of the medical vest on the user's body.

8. The method according to claim 7, wherein the at least one body message comprises at least one of the following: body height of the user, body weight of the user, age of the user and gender of the user.

9. The method according to claim 7, further comprising:
in step a), repeatedly using a specific vibration device of the at least one vibration device to provide different vibration forces during a test period in sequence and using the motion sensor in the medical vest to detect the vibration frequency and/or the vibration intensity of each vibration force provided by the specific vibration device;
in step b), using the transmission module placed in the medical vest to transmit each detected message detected during each test period to the control device; and
in step c), choosing a specific vibration force based on a human body sense of the user wearing the medical vest and/or an evaluation result of a medical professional, and also using the control device to set up the specific vibration device to continuously provide the chosen specific vibration force during a medical period, and then using the control device to set up the specific vibration device to continuously provide an adjusted specific vibration force during a medical period when the corresponding vibration frequency and/or vibration intensity is adjusted initially after the specific vibration force is chosen.

10. The method according to claim 9, further comprising using the control device to set up the at least one vibration device corresponding to one or multiple specific portions of the user's body after the control device receives a message which is sent from an intelligent stethoscope and indicates the one or multiple specific portions of the user's body having at least one of the following: sputum, mucus, and debris.

11. A method of using a medical vest, comprising:
a) using a motion sensor placed in the medical vest to detect an initial body posture message when a user initially wears the medical vest;

b) using the motion sensor to detect another body posture message when the user adjusts his body posture so that the medical vest applies vibration force to the user's chest cavity; and
c) determining whether the user has adjusted his body posture to a particular thoracic therapy posture according to the body posture, a gravity force, a magnetic force and an acceleration detected by the motion sensor, wherein each of the gravity force, magnetic force and acceleration are detected in x, y and z coordinate directions,
b) using the motion sensor to detect another one body posture message when the user adjusts his body posture so that the medical vest applies vibration force to the user's chest cavity; and
c) determining whether the user has adjusted his body posture to a special thoracic therapy posture according to the body posture, a gravity force, a magnetic force and an acceleration on every direction detected by the motion sensor.

12. The method according to claim 11, further comprising attaching twelve chest physical therapy posture icons and a table of recommended motion sensor values to a cloth of the medical vest, so as to provide reference to a user when he wants to adjust his body posture to a specific chest therapy posture after wearing the medical vest.

* * * * *